KOREAN MOUNTAIN ASH TREE
Filed May 8, 1972
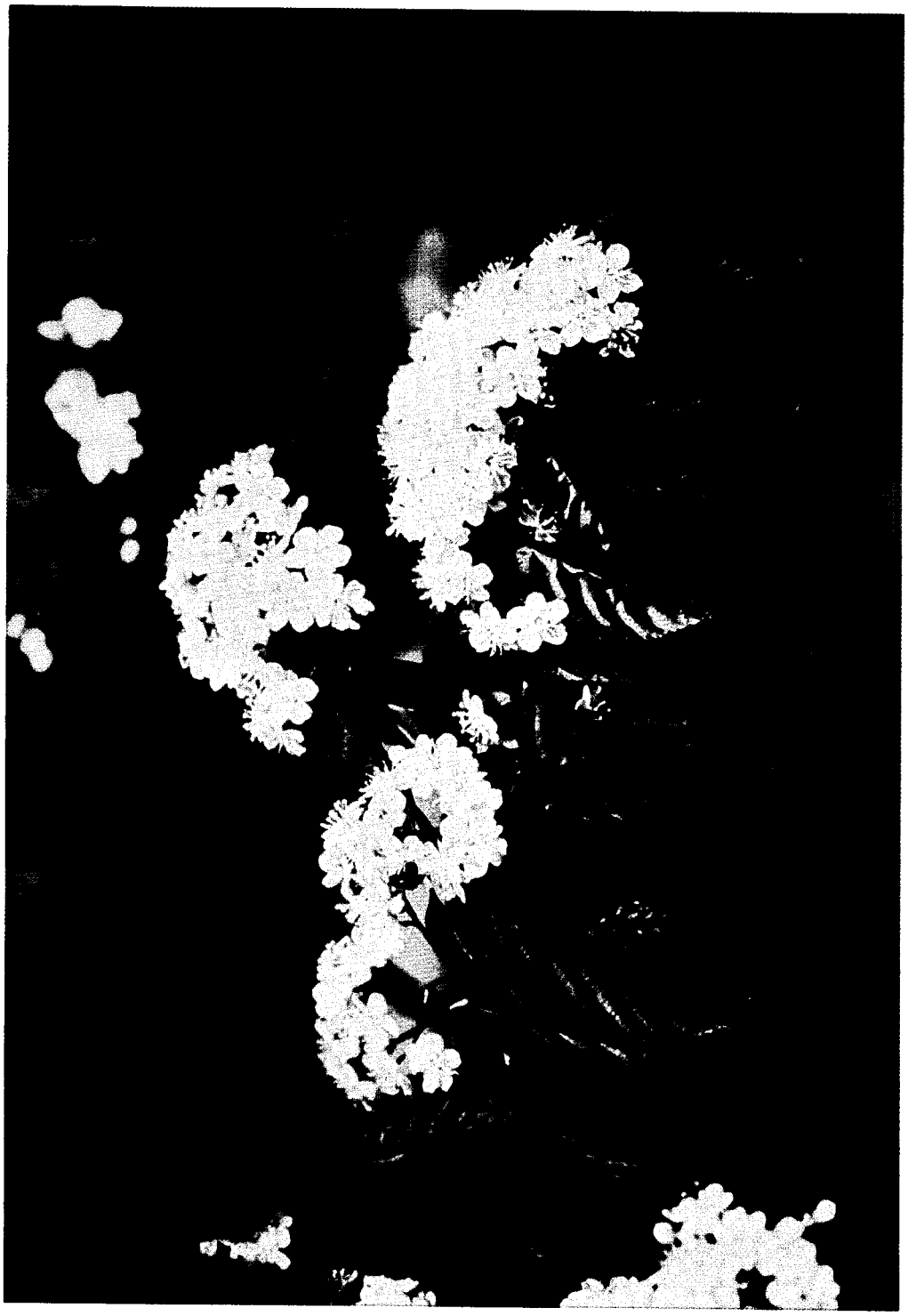

KOREAN MOUNTAIN ASH TREE
Filed May 8, 1972 2 Sheets-Sheet 2
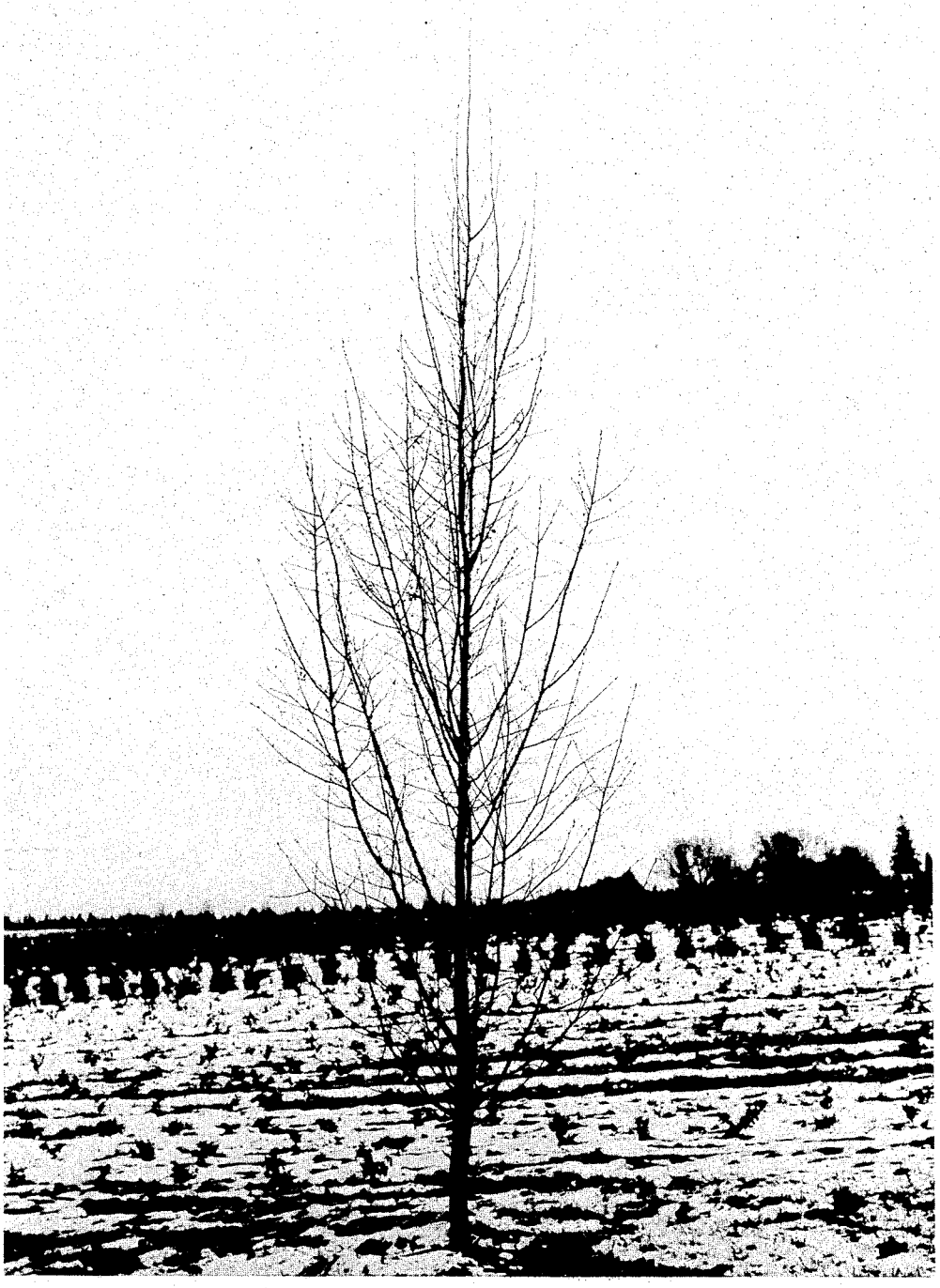

United States Patent Office

Plant Pat. 3,400
Patented Sept. 18, 1973

3,400
KOREAN MOUNTAIN ASH TREE

William Flemer III, Princeton, N.J., assignor to Treesearch, Kingston, N.J.

Filed May 8, 1972, Ser. No. 251,499
Int. Cl. A01h *5/12*
U.S. Cl. Plt.—51 1 Claim

The present invention relates to a new and distinct variety of mountain ash tree of the Korean mountain ash species botanically known as *Sorbus alnifolia,* which was discovered by me as a selected cultivated seedling mutation of unknown parentage among a group of nursery plants of the mountain ash variety known as "Rochester" which were being grown under my direction and supervision in Plainsboro Township, N.J.

My attention was first attracted to the new seedling among a row of seedlings of the "Rochester" variety because of its exceptionally vigorous habit of growth. At that time, the new seedling was 27 inches tall, while the adjacent seedlings were only 12 to 16 inches tall. I then planted out the new seedling in wide spacing and grew it on with the others of the best seedlings of this particular crop and with the crops of the next 2 years. Continued close observations of the new seedling and of progeny thereof subsequently asexually propagated by me in Plainsboro Township, N.J. for a prolonged period of years, confirmed that the exceptionally vigorous habit of growth of the new seedling was an established feature thereof, among other distinctive features observed during my tests. I am, therefore, convinced that my new seedling represents a new and improved variety of mountain ash, as particularly evidenced by the following unique combination of characteristics which are outstanding therein and which distinguish it from the "Rochester" variety and from all other varieties of this species:

(1) An exceptionally vigorous habit of growth;

(2) A narrow-oval and very upright tree form in comparison with the normal habit of Korean mountain ash trees which are more spreading and often drooping in habit;

(3) Thick and leathery leaves which are very resistant to physiological leaf scorch in hot weather;

(4) Showy clusters of white flowers which bloom in the month of May in New Jersey;

(5) Heavily borne bright red fruits which last late into the winter season without losing their color; and (6) Especial suitability for street tree plantings where pedestrian and vehicle clearance is essential.

Asexual reproduction of my new variety by grafting, as performed by me in my nursery located in Plainsboro Township, N.J., shows that the foregoing characteristics and distinctions come true and are established and transmitted through succeeding propagations.

The accompanying drawings show a typical bare tree specimen of my new variety depicting its narrow-oval and very upright form, and also show typical foilage and flower specimens as depicted in color.

The following is a detailed description of my new variety of Korean mountain ash tree, with color terminology in accordance with the Nickerson Color Fan, published by Munsell Color Co., Inc., of Baltimore, Md., except where general color terms of ordinary dictionary significance are obvious:

Parentage: A selected seedling mutation of unknown parentage.

Propagation: Holds its distinguishing characteristics through succeeding propagations by grafting.

Locality where grown and observed: Plainsboro Township, N.J.

Tree: Large for the species; very upright; tall, narrow-oval forms; dense; hardy.

*Trunk.*—Stocky; smooth.

*Branches.*—Stocky; smooth. Color—Brownish Gray, Hue 10 YR 3/1. Lenticels—moderately abundant; large; flat.

Foliage:

*Leaves.*—Thick; leathery; abundant.

*Size.*—Length of blade—from 7 cm. to 8 cm. Width—from 4.5 cm. to 4.6 cm.

*Shape.*—Ovate-acuminate.

*Color.*—Upper surface—Dark Green, Hue 7.5 G 3/6. Under surface—Strong Yellowish Green, Hue 2.5 G 6/9.

*Margin.*—Doubly serrate.

*Petiole.*—Medium length (about 2.5 cm.).

*Glands.*—None.

*Stipules.*—Short (about 0.5 cm.).

Flowers buds:

*Hardiness.*—Very hardy.

*Size.*—About 0.8 cm. long.

*Shape.*—Narrow-ovate; pointed at the top.

*Color.*—Moderate Brown, Hue 7.5 YR 4/5.

Flowers:

*Borne.*—In umbellate clusters of from 28 to 32 flowers per cluster.

*Bloom dates.*—First bloom—about May 15 (in New Jersey). Full bloom—about May 20 (in New Jersey).

*Quantity.*—Abundant.

*Size.*—Large (about 1.5 cm. in diameter).

*Pistil.*—Bifurcate.

*Stamens.*—12 or 13 in number; each stamen about 0.5 cm. long.

Petalage:

*Number of Petals.*—5.

*Shape.*—Oval.

*Size.*—Length—about 0.5 cm. Width—about 0.6 cm.

*Color.*—White, with center of Brilliant Greenish Yellow, Hue 10 Y 9/9.

Fruits:

*Borne.*—In drooping clusters of from 14 to 18 fruits per cluster.

*Ripening habit.*—Ripen and color up in early October in New Jersey.

*Quantity.*—Very abundant.

*Shape.*—Oval with flat ends.

*Size.*—Length—about 1.25 cm. Width—about 0.9 cm.

*Color.*—Dark Reddish Orange, Hue 7.5 R 4/12 at first, becoming Strong Red, Hue 5 R 4/12 after frosts and cold weather.

I claim:

1. A new and distinct variety of mountain ash tree of the Korean mountain ash species botanically known as *Sorbus alnifolia,* substantially as herein shown and described, characterized particularly as to novelty by the unique combination of an exceptionally vigorous habit of growth, a narrow-oval and very upright tree form in comparison with the normal habit of Korean mountain ash trees which are more spreading and often drooping in habit, thick and leathery leaves which are very resistant to physiological leaf scorch in hot weather, showy clusters of white flowers which bloom in the month of May in New Jersey, heavily borne bright red fruits which last late into the winter season without losing their color, and especial suitability for street tree plantings where pedestrian and vehicle clearance is essential.

No references cited.

ROBERT E. BAGWILL, Primary Examiner